United States Patent [19]

Webster

[11] Patent Number: 4,692,417

[45] Date of Patent: Sep. 8, 1987

[54] IMMUNOLOGICAL IDENTIFICATION TEST FOR GROUP D STREPTOCOCCI USING ACHROMOPEPTIDASE

[75] Inventor: Martyn F. Webster, Basingstoke, England

[73] Assignee: Oxoid Limited, Hampshire, England

[21] Appl. No.: 739,462

[22] Filed: May 30, 1985

[30] Foreign Application Priority Data

Jun. 5, 1984 [GB] United Kingdom ................. 8414273

[51] Int. Cl.[4] ...................... G01N 33/53; C12Q 1/38; C12Q 1/14
[52] U.S. Cl. ................................... 436/518; 436/533; 435/7; 435/23; 435/36
[58] Field of Search ............... 435/7, 23, 36; 436/518, 436/533

[56] References Cited

U.S. PATENT DOCUMENTS 4,264,766  4/1981  Fischer ............................... 436/533
4,626,502  12/1986  Krause-Hooyman ................. 435/23

FOREIGN PATENT DOCUMENTS 0109012  5/1984  European Pat. Off. .
0151783  8/1985  European Pat. Off. .
0153477  9/1985  European Pat. Off. .
1268173  3/1972  United Kingdom .

OTHER PUBLICATIONS

Maxted, "The Lancet", pp. 255–256 (1948).
Masaki et al., "Biochimica et Biophysica Acta" 660, 44–50, 151–55 (1981).
Chang et al., "J. Clin. Microbiology" 17(5) 804–806, May 1983.
Levchak et al., "J. Clin. Microbiology 15(1) 58–60, Jan. 1982.
Birch et al., "The Lancet", p. 856, Apr. 14, 1984.
T. Ezaki and S. Suzuki, J. Clin. Microbiol. vol. 16(5), pp. 844–846, Nov. 1982.
R. R. Facklam in CRC. Crit. Rev. Clin. Lab. Sci., vol. 6 (4), pp. 287–317 (1976).
L. Krause–Hooyman et al., Abstracts of Annual Meeting of Amer. Soc. Microbiol., (1984).
C. A. Waters et al., J. Clin. Microbiol., vol. 5 (2), 255–6 (1977).
M. W. Keville et al., J. Clin. Microbiol., vol. 16 (1), 92–5 (1982).

Primary Examiner—Christine M. Nucker
Assistant Examiner—Stephen C. Wieder
Attorney, Agent, or Firm—Cushman, Darby & Cushman

[57] ABSTRACT

The grouping of a sample of a streptococcus is identified by treating the sample with achromopeptidase prior to contacting the sample with a group-specific antibody bound to minute, insoluble carrier particles. A positive identification is indicated by agglutination of the carrier particles.

18 Claims, No Drawings

IMMUNOLOGICAL IDENTIFICATION TEST FOR GROUP D STREPTOCOCCI USING ACHROMOPEPTIDASE

The present invention relates to a method for identifying the serological grouping of streptococci. It is very important, clinically, to identify the group to which a particular streptococcus belongs.

Conventionally, streptococcal grouping is identified by extracting the group specific antigens from the cells of the streptococcus, mixing the group specific antigens with antibodies specific to each of the Lancefield groups A,B,C,D, F and G and then inspecting each antigen/antibody mixture for agglutination to indicate the occurrence of an antigen-antibody reaction. Observation of agglutination is conventionally facilitated by the use of group-specific antibodies bound to minute particles of a carrier material, such as polystyrene latex, which minute particles are suspended in the liquid in which the test is being carried out. The group specific antigens are extracted or released from the streptococcus cell walls, so that they are available for reaction with the group specific antibodies, by subjecting the streptococcus cells to the action of certain proteolytic enzymes. Examples of proteolytic enzymes utilized for this purpose include trypsin, lysozyme and pronase, an enzymic preparation obtained from *Steptomyces griseus* generally known as Maxted enzyme after W. R. Maxted who discovered it (see "The Lancet", Aug. 14, 1948m pp 255-256). Unfortunately, there are a number of problems associated with the use of these conventional enzymes. For instance, trypsin has been found to have no effect on group D streptococci (M. E. Levchak and P. D. Ellner, J. Clin. Microbiol. 15 1982, pp 58-60). The action of lysozyme is such that one may obtain non-specific results. In latex agglutination tests, i.e. where the group specific antibody is bound to minute polystyrene latex particles, in suspension, lysozyme causes non-specific clumping of the latex particles to occur. (G. T. Chang and P. D. Ellner, J. Clin. Microbiol., 17, No. 5, pp 804-806). Pronase extracts group antigens of Lancefield groups A,B,C, G and F very well but is rather less effective in exposing D antigen from group D streptococci. This can be a problem if the streptococcus contains group D antigen and another group antigen. In such a case, the agglutination test would indicate a stronger reaction of the antigen with the antibody specific to the other group than with the group D specific antibody. Thus the streptococcus may be mistakenly identified and lead to incorrect diagnosis. This problem has been recognized with strains of *Streptococcus faecalis* containing group G, as well as group D, antigen ("The Lancet", Apr. 14, 1984, page 856).

We have found that the disadvantages associated with the use of the prior art enzymes do not arise with the use of achromopeptidase to expose the streptococcal antigen sites.

The present invention provides a method for identifying the grouping of a streptococcus which method comprises treating sample of the streptococcus with achromopeptidase, contacting the treated sample with group-specific antibody bound to minute, insoluble carrier particles and examining the mixture for agglutination.

Achromopeptidase in the name given to the bacteriolytic enzyme obtained from *Achromobacter lyticus* which is disclosed in GB 1,268,173. The proteolytic activity of achromopeptidase has been the subject of a number of studies, see Biochimica et Biophysica Acta, 660 (1981) pp 44-50 and pp 51-55 and also J. Clin. Microbiology, 16 (1982) No. 5. pp 844-846. Although achromopeptidase has known bacteriolytic activity, we have discovered that it releases group antigens from streptococci such that they remain immunologically active. Furthermore, unlike some bacteriolytic agents which give non-specific results e.g. lysozyme and N-acetylmuramidase SG, the use of achromopeptidase allows easy and specific identification of group antigens. In addition, achromopeptidase has the surprising advantage over previously used extraction enzymes in that it releases group D antigens from streptococci cells quickly. Thus, by using achromopeptidase in streptococcal grouping tests, fast and correct identification of group D streptococci can be achieved.

The present invention further provides a kit for use in the above-described method for identifying the grouping of a streptococcus comprising:

(1) achromopeptidase; and
(2) carrier-bound antibody specific to each antigenic group.

In order to facilitate observation of any agglutination reaction, the group-specific antibodies are bound to minute carrier particles which are in suspension in the liquid medium in which the tests are carried out. Minute particles of polystyrene latex, bacteria or charcoal are conventionally used as carriers for the antibody and are suitable for use in the present invention. Typically, the carrier particles may be coloured in order to facilitate further the observation of agglutination. Methods of binding the group-specific antibodies are known in the art and need not be further discussed here.

A kit will usually comprise, in separate containers, a latex reagent for each of the Lancefield groups A, B, C, D, F and G wherein each latex reagent comprises a suspension of the carrier-bound antibody specific to a particular antigenic group; a positive control containing extracts from all six of the group antigens; and achromopeptidase. Preferably, the achromopeptidase contains a preservative, such as thiomersal. Also the latex reagents and the positive control will typically contain a preservative, for example, sodium azide.

Usually, a sample of the streptococcus to be identified is taken from an infected area and cultured and the suspected offending bacteria, are then extracted and treated with a solution of achromopeptidase made up in 0.01M Tris-HCl, pH 8.0. The mixture may then be incubated overnight at 4° C. or alternatively for 5-15, preferably 10 minutes at a temperature of from about 37° to 56° C. A drop of the resulting mixture is then placed on a glass slide and mixed with the grouping reagent containing a homogeneous suspension of carrier particles bound or coated with antibody specific to a particular antigenic group. The glass slide test is repeated for each grouping reagent for each of groups, A, B, C, D, F and G. Each slide is gently rocked and then examined for agglutination.

COMPARATIVE EXAMPLE 1.

Latex agglutination tests were carried out to identify the group antigen of streptococci classified in each of the Lancefield groups A,B,C,D, F and G, using different extraction enzymes. The enzymes used were as follows:

OA: Oxoid reagent using achromopeptidase (obtained from Takeda Chemical Industries Ltd. Japan) made up in 0.01M Tris-HCl pH 8.0.

WSP: "STREPTEX" (Wellcome Diagnostics) which uses pronase

OSP: Oxoid reagent using SIGMA PROTEASE (pronase from Sigma Chemicals Co., USA) made up in 0.1M phosphate buffered saline pH 7.4.

OSL: Oxoid reagent using SIGMA LYSOZYME (lysozyme from Sigma Chemicals Co., USA) made up in 0.1M phosphate buffered saline, pH 7.4.

OBP: Oxoid reagent using B.D.H. Pronase made up in 0.1M phosphate buffered saline pH 7.4.

The results are shown below wherein

| EXTRACTION ENZYME | A | B | C | D | G | F |
|---|---|---|---|---|---|---|
| GROUP 'A' | | | | | | |
| OA | ++++ | − | − | − | − | − |
| WSP | ++ | − | − | − | − | − |
| OSP | +++ | + | − | + | + | + |
| OSL | + | − | + | + | ++++ | − |
| OBP | +++ | + | − | + | − | + |
| GROUP 'B' | | | | | | |
| OA | − | ++++ | − | − | − | − |
| WSP | − | ++++ | − | − | − | − |
| OSP | − | ++++ | + | + | − | − |
| OSL | − | ++++ | ++ | +++ | + | + |
| OBP | − | ++++ | + | +++ | − | − |
| GROUP 'C' | | | | | | |
| OA | − | − | ++++ | − | − | − |
| WSP | − | − | ++++ | − | − | − |
| OSP | − | − | ++++ | − | − | − |
| OSL | + | ++ | ++++ | − | + | + |
| OBP | − | − | ++++ | + | − | − |
| GROUP 'D' | | | | | | |
| OA | − | − | − | +++ | − | − |
| WSP | − | − | − | +++ | − | − |
| OSP | − | − | − | +++ | − | + |
| OSL | +++ | − | + | +++ | + | +++ |
| OBP | − | − | − | +++ | − | + |
| GROUP 'G' | | | | | | |
| OA | − | − | − | − | ++++ | − |
| WSP | − | − | − | − | ++++ | − |
| OSP | − | − | − | + | ++++ | − |
| OSL | ++ | ++ | + | ++ | ++++ | + |
| OBP | − | − | − | + | ++++ | − |
| GROUP 'F' | | | | | | |
| OA | − | − | − | − | − | ++++ |
| WSP | − | − | − | − | − | ++++ |
| OSP | − | − | − | + | − | ++++ |
| OSL | ++ | ++ | ++ | ++ | ++ | ++++ |
| OBP | − | + | + | − | − | ++++ |

++++ denotes a strong positive reaction
++ denotes a positive reaction
+ denotes a weak positive reaction
− denotes no reaction.

N.B. We also tried n-Acetylmuramidase SG enzyme from *Streptomyces globisporus* as an extraction enzyme but we found that this gave agglutination in all extracts tried.

COMPARATIVE EXAMPLE 2

Latex agglutination tests were carried out to identify the group antigens of 22 streptococcal strains classified biochemically as group D but which contain G group antigens in addition to D group antigens (cf. "The Lancet", Apr. 14, 1984, page 856). The reagents used were the Oxoid latex reagent using achromopeptidase (Takeda Chemical Industries Ltd) made up in 0.01M Tris-HCl, pH 8.0, as the extraction enzyme and "STREPTEX" (Wellcome Diagnostics) with pronase as the extraction enzyme. Out of 22 strains tested, the Oxoid reagent using achromopeptidase correctly identified all 22 as strains classified biochemically as group D and identified the presence of group G antigen in 7 of the strains. We found that, with "STREPTEX", agglutination for group G appeared first followed by agglutination for group D. However, with the Oxoid reagent using achromopeptidase, D agglutination appears before G agglutination. Although the "STREPTEX" grouping kit identified the presence of D and G group antigens in all 22 strains, the order in which it did this could lead to confusion or misidentification of the Lancefield grouping.

I claim:

1. An immunological agglutination test method for identifying Lancefield group D streptococcus, which comprises treating a sample suspected of containing group D streptococcus with achromopeptidase, contacting the sample with antibody specific for Lancefield group D streptococcal antigen to form a mixture, said antibody being bound to minute, insoluble carrier particles and examining the mixture for agglutination as an indication of the presence of Lancefield Group D streptococci.

2. The method according to claim 1, wherein the sample of the streptococcus and the achromopeptidase are incubated overnight at 4° C.

3. The method according to claim 1, wherein the sample of the streptococcus and the achromopeptidase are incubated at a temperature of from 37° to 56° C. for from 5 to 15 minutes.

4. The method according to claim 1, wherein the achromopeptidase is used in the form of a solution of 0.01M Tris-HCl having pH 8.0.

5. The method according to claim 1, wherein group-specific antibody is bound to minute particles of polystyrene latex, bacteria or charcoal.

6. A kit for use in the method of claim 1, comprising
   (1) achromopeptidase; and
   (2) carrier-bound antibody specific to Lancefield Group D streptococcus.

7. The kit according to claim 6, wherein the achromopeptidase is provided in a solution of 0.01M Tris-HCl having pH 8.0.

8. The kit according to claim 7, wherein the achromopeptidase solution contains one or more preservatives.

9. An immunological agglutination test method for distinguishing streptococci of Lancefield groups D and G, which comprises treating a sample suspected of containing streptococcus of group D or G with achromopeptidase, contacting respective portions of the treated sample with respective antibodies specific for Lancefield group D or G streptococcal antigen respectively, to form a mixture for each group, each said antibody being bound to a respective portion of minute, insoluble carrier particles and examining each mixture for agglutination.

10. The method according to claim 9, wherein the sample of the streptococcus and the achromopeptidase are incubated overnight at 4° C.

11. The method according to claim 9, wherein the sample of the streptococcus and the achromopeptidase are incubated at a temperature of from 37° to 56° C. for from 5 to 15 minutes.

12. The method according to claim 12, wherein the achromopeptidase is used in the form of a solution of 0.01M Tris-HCl having pH 8.0.

13. The method according to claim 12, wherein group-specific antibody is bound to minute particles of polystyrene latex, bacteria or charcoal.

14. A kit for use in an immunological agglutination test method for distinguishing streptococci of Lancefield Groups D and G, comprising, in separate containers,
   (1) anchromopeptidase; and
   (2) carrier-bound antibodies respectively specific to each of the antigenic groups D and G.

15. The kit according to claim 14, comprising, in separate containers, a latex reagent for each of Lancefield groups D and G wherein each latex reagent comprises a suspension of minute particles of polystyrene latex bound to antibody specific to one of said groups; a positive control containing extracts from each of the group antigens; and achromopeptidase.

16. The kit according to claim 14, wherein the achromopeptidase is provided in a solution of 0.01M Tris-HCl having pH 8.0.

17. The kit according to claim 16, wherein the achromopeptidase solution contains one or more preservatives.

18. The kit according to claim 15, wherein the latex reagents and the positive control contain one or more preservatives.

* * * * *